US00PP22999P3

(12) United States Plant Patent
Korlipara

(10) Patent No.: US PP22,999 P3
(45) Date of Patent: Aug. 28, 2012

(54) ***ECHINACEA* PLANT NAMED 'SATIN NIGHTS'**

(50) Latin Name: *Echinacea purpurea*
Varietal Denomination: Satin Nights

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 81 days.

(21) Appl. No.: 12/931,232

(22) Filed: Jan. 26, 2011

(65) Prior Publication Data

US 2012/0192325 P1 Jul. 26, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Satin Nights' characterized by numerous medium size, rose purple inflorescences, a compact, dwarf habit, dark stems, and excellent vigor.

1 Drawing Sheet

Botanical denomination: *Echinacea purpurea.*
Variety designation: 'Satin Nights'.

The present invention relates to a new and distinct cultivar of *Echinacea purpurea* and given the cultivar name 'Satin Nights'. *Echinacea* is in the family Asteraceae. This new cultivar originated from a planned breeding project for a dwarf plants using proprietary, unnamed *Echinacea.* Its exact parents are unknown. *Echinacea* 'Satin Nights' was selected for its dark stems and dwarf habit.

Compared to *Echinacea* 'Emily Saul', U.S. Plant Pat. No. 18,768, the new cultivar is shorter and has ray florets that are lighter and more perpendicular to the stem.

These characteristics in combination distinguish 'Satin Nights' as a new and distinct cultivar of *Echinacea:*

1. numerous, medium size, rose purple inflorescences,
2. compact, dwarf habit,
3. dark stems,
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the habit of one-year-old *Echinacea* 'Satin Nights' growing in the ground in the trial field in Canby, Oreg.

FIG. 2 shows a close up of the inflorescences later in the summer.

DETAILED PLANT DESCRIPTION

The following is a detailed description of the new *Echinacea* cultivar based on observations of 18-month-old specimens growing in the ground in the field in full sun in the trial bed under typical outdoor conditions in Canby, Oreg. The plants had been moved from one trial field to another the fall before. Canby is in Zone 8 on the USDA Hardiness map Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, fifth edition.

Plant:

*Type.*—Herbaceous perennial.
*Hardiness.*—USDA Zones 4 to 9.
*Size.*—Grows to 45 cm wide and 47 cm tall to top of inflorescences.
*Form.*—Basal clump.
*Vigor.*—Excellent.
*Roots.*—Roots develop easily from cuttings from the crown.

Stem (flowering):

*Type.*—Ascending, most unbranched, few branching 1 to 2 times.
*Size.*—Grows to 24.5 cm tall (to the upper most leaves) and 4 mm wide at base.
*Number of stems from the crown.*—30 to 40.
*Internode length.*—2 to 5.5 cm.
*Surface texture.*—Strigose.
*Color.*—Greyed Purple 187A in sun and Yellow Green 148A in shade.

Leaf (basal):

*Type.*—Simple.
*Shape.*—Ovate to lanceolate.
*Arrangement.*—Basal.
*Blade size.*—Grows to 15 cm long and 7 cm wide.
*Margins.*—Coarsely serrate.
*Apex.*—Acute.
*Base.*—Attenuate.
*Surface texture.*—Strigose on both sides.
*Venation.*—Pinnate.
*Color.*—Topside, closest to Green 137A and bottom side closest to Green 137B.

*Petiole description.*—Grows to 14.5 cm long and 3 mm wide, glabrous, Yellow Green 148C except topside base where Greyed Purple 187A.

Leaf (stem):

*Type.*—Simple.

*Shape.*—Ovate to lanceolate.

*Arrangement.*—Alternate.

*Blade size.*—Grows to 10 cm long and 3.5 cm wide.

*Margins.*—Coarsely serrate.

*Apex.*—Acute to acuminate.

*Base.*—Attenuate, continuing down petiole, clasping.

*Surface texture.*—Strigose on both sides.

*Venation.*—Pinnate.

*Color.*—Topside, Green 137A, bottom side closest to Yellow Green 147B.

*Petiole description.*—Grows to 4 cm long on lower leaves and 5 mm wide, glabrous to slightly strigose, Yellow Green 146C tinted Greyed Purple 187A.

Inflorescence:

*Type.*—Composite on terminal stalked heads.

*Number of flowering stems per plant in summer.*—30 to 40 from the crown, some branching.

*Flowering stem.*—Grows to 24.5 cm tall from the base of the plant to the terminal inflorescence and can grow to 10.5 cm long from the top leaf to the base of a inflorescence; branched, 1 to 3 inflorescences per stem; diameter growing to 1 cm wide near the inflorescence; strigose, Greyed Purple 187A in sun and Yellow Green 148A in shade.

*Size.*—Grows to 10 cm wide and 2.5 cm deep as disc enlarges.

*Form.*—Ray florets held perpendicular to the stem, mature disc is conic.

*Immature inflorescence.*—4 cm wide and 3.7 cm deep, ray florets held at a 50 degree angle and rolled up so only the back color shows, Greyed Purple 187B with Yellow Green 150C near tip, disc closest to Brown 200A.

*Ray florets.*—Without pistil or stamen, 23 to 31 in number, oblanceolate with the tip 2 to 3 toothed (each acute), entire margins, base attenuate, grows to 4 cm long and 1 cm wide, glabrous on both sides; topside Red Purple 62A at base lightening to Greyed Purple 186C near the tip, bottom side Greyed Purple 186B to Greyed Purple 186C.

*Disc.*—Slightly convex becoming conic, becoming 1.8 cm deep and 3 cm wide with maturity, Greyed Purple 187A to 187B.

*Disc florets.*—About 200 in number, with pistil and stamen, each 10 mm long and 1.1 mm wide, each with one persistent, very stiff bract (11 mm long, Greyed Purple 187A on the tip, Orange 29A on the top ⅓, Yellow Green 146C on middle ⅓, White 155B on bottom ⅓); corolla 4.5 mm long and 1.1 mm wide, 5 lobed, glabrous, Yellow Green 146C on base and changing to Greyed Purple 187A on tip, pistil 10 mm long, ovary 2.5 mm long, White 155C, style 5 mm long, Yellow Green 147D, with an extruding, 2-branched stigma spreading 2 mm wide, Greyed Purple 187A; stamen 4 in number, 5 mm long, anthers 3 mm long and Greyed Purple 187A, filaments 2 mm long, Yellow Green 147D, pollen Yellow Orange 18A.

*Phyllaries.*—In 4 leafy series, area 30 mm wide and 11 mm deep, lobes lanceolate in shape, reflexed, grow to 11 mm long and 3 mm wide, surface strigose, tip acute, Yellow Green 147A.

*Receptacle.*—Grows to 8 mm wide and 12 mm deep, White 155B, except top surface Greyed Purple 185C.

*Bloom period.*—July through October in Canby, Oreg.

*Fragrance.*—Nice, sweet.

*Lastingness.*—Each inflorescence lasts about two weeks in Canby, Oreg.

Seeds: Few, 5 mm long, triangular, Grey Brown N199A.

*Fertility.*—Low.

Disease and pests: *Echinacea* are susceptible to leaf miners, powdery mildew, bacterial spots, and gray mold. None of these have been observed on plants grown under commercial conditions in Canby, Oreg. No resistance is know.

I claim:

1. A new and distinct *Echinacea* plant as herein illustrated and described.

* * * * *

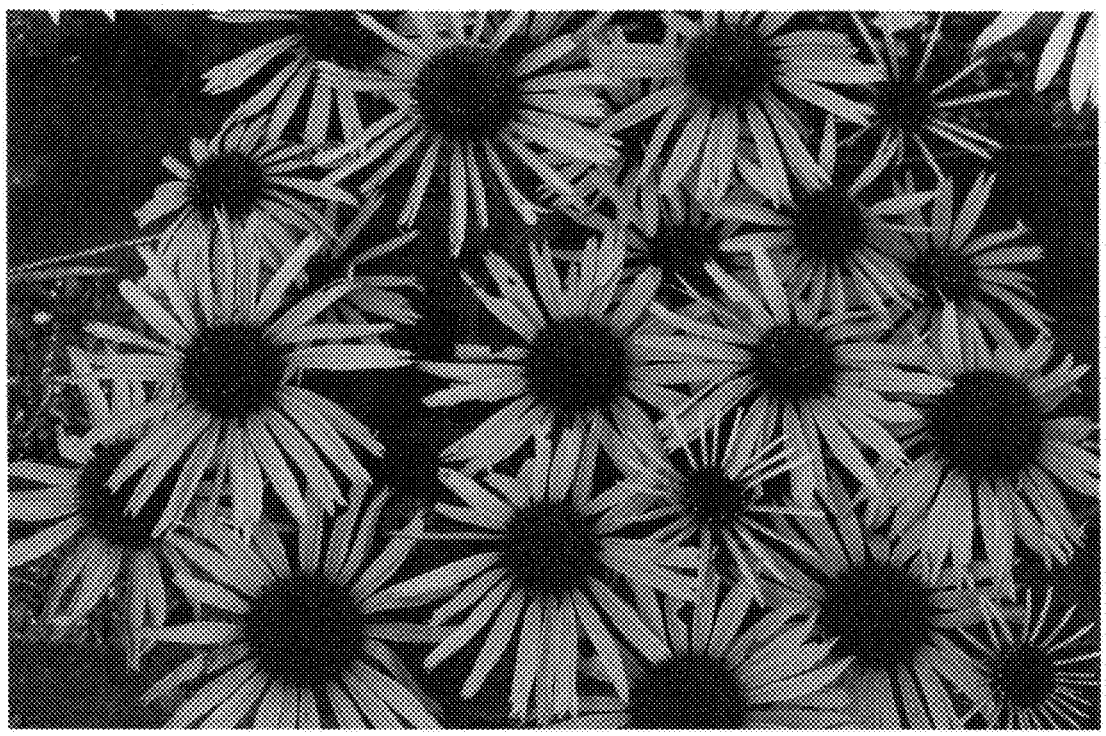

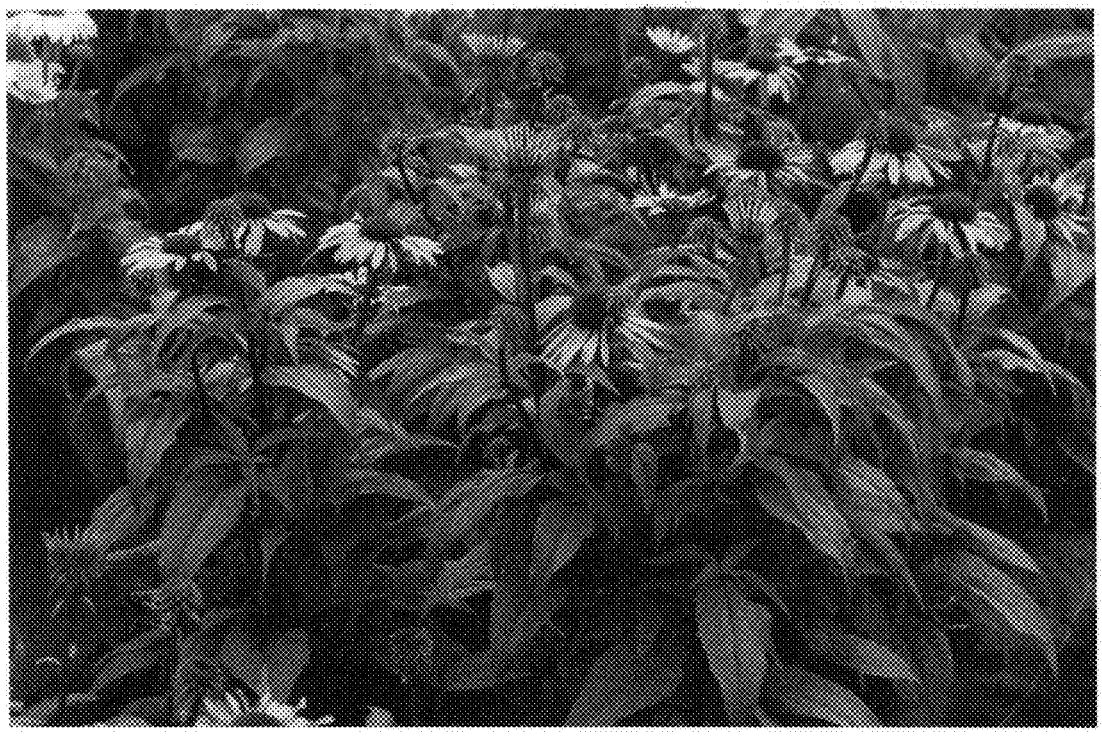
Figure 1 above
Figure 2 below